(12) United States Patent
Dahlgren

(10) Patent No.: US 7,198,622 B2
(45) Date of Patent: Apr. 3, 2007

(54) DIAPER HAVING REFASTENABLE SIDE-BRIDGING JOINS

(75) Inventor: Marie Dahlgren, Göteborg (SE)

(73) Assignee: SCA Hygiene Products AB, Gothenburg (SE)

( * ) Notice: Subject to any disclaimer, the term of this patent is extended or adjusted under 35 U.S.C. 154(b) by 563 days.

(21) Appl. No.: 10/335,866

(22) Filed: Jan. 3, 2003

(65) Prior Publication Data

US 2003/0158535 A1    Aug. 21, 2003

Related U.S. Application Data

(60) Provisional application No. 60/352,580, filed on Jan. 31, 2002.

(51) Int. Cl.
*A61F 13/15* (2006.01)

(52) U.S. Cl. .............. 604/386; 604/391; 604/392

(58) Field of Classification Search ........... 604/391, 604/386, 385.04, 385.23–385.3, 392, 389–390; 24/304; D24/206, 124
See application file for complete search history.

(56) References Cited

U.S. PATENT DOCUMENTS

| | | | | |
|---|---|---|---|---|
| 2,288,893 A * | 7/1942 | Elofson | ............... | 604/392 |
| 2,564,094 A * | 8/1951 | Brandl | ............... | 604/392 |
| 2,743,725 A * | 5/1956 | Matthews | ........... | 604/392 |
| 2,931,747 A * | 4/1960 | Dexter | ................ | 428/57 |
| 3,386,442 A * | 6/1968 | Sabee | ................ | 604/366 |
| 4,555,244 A * | 11/1985 | Buell | ................ | 604/392 |
| 4,680,030 A * | 7/1987 | Coates et al. | ........ | 604/391 |
| 5,031,248 A * | 7/1991 | Kemper | ............... | 2/406 |
| 5,142,743 A * | 9/1992 | Hahn | ................ | 24/16 R |
| 5,176,671 A * | 1/1993 | Roessler et al. | .... | 604/391 |
| 5,368,585 A * | 11/1994 | Dokken | .............. | 604/393 |
| 5,545,159 A * | 8/1996 | Lancaster et al. | ..... | 604/391 |
| 5,603,794 A * | 2/1997 | Thomas | .............. | 156/256 |
| 5,611,789 A * | 3/1997 | Seth | ................ | 604/391 |
| 5,690,627 A * | 11/1997 | Clear et al. | ........ | 604/385.29 |
| 5,695,488 A * | 12/1997 | Sosalla | ............ | 604/385.24 |
| 5,722,127 A * | 3/1998 | Coates | .............. | 24/304 |
| 5,989,236 A * | 11/1999 | Roe et al. | ........ | 604/385.04 |
| 6,520,947 B1 * | 2/2003 | Tilly et al. | ........ | 604/391 |
| 6,911,023 B1 * | 6/2005 | Hamilton et al. | ..... | 604/387 |
| 2002/0095130 A1 * | 7/2002 | Seitter et al. | ..... | 604/389 |
| 2005/0059947 A1 * | 3/2005 | Murguly | ............ | 604/387 |

FOREIGN PATENT DOCUMENTS

| | | | |
|---|---|---|---|
| WO | 97/13485 | | 4/1997 |
| WO | WO 00/23025 | * | 4/2000 |
| WO | 00/35399 | | 6/2000 |
| WO | 00/37009 | | 6/2000 |

* cited by examiner

*Primary Examiner*—Tatyana Zalukaeva
*Assistant Examiner*—Ginger Chapman
(74) *Attorney, Agent, or Firm*—Buchanan Ingersoll & Rooney, PC

(57) ABSTRACT

A pant diaper or diaper whose side edges are joined to form a pants-like shape with the help of strips provided with interacting hook and loop devices respectively that extend along the long edges of the front and rear sections. The edges of the strips that face the legs are covered by a band of soft and flexible material.

15 Claims, 3 Drawing Sheets

DIAPER HAVING REFASTENABLE SIDE-BRIDGING JOINS

CROSS-REFERENCE TO RELATED APPLICATIONS

The present application claims the benefit of U.S. Provisional Application No. 60/352,580, filed in the United States on Jan. 31, 2002, the entire contents of which are hereby incorporated herein by reference.

TECHNICAL FIELD

The present invention relates to a diaper or pant diaper with a front section, a rear section, and an intermediate crotch section that has a narrower width than the front and rear sections, plus a longitudinal line of symmetry that extends from the middle of the rear edge of the rear section to the middle of the front edge of the front section, where the diaper or pant diaper includes an absorption body that is enclosed between an inner surface layer of liquid-permeable material and an outer surface layer of liquid-impermeable material, whereby the side parts of the front and rear sections are joinable to one another with a refastenable closure by means of a first mechanical join so that the diaper or pant diaper, in the position of use where the side parts are joined to one another in an over-lapping manner, acquires a pants-like configuration with one waist opening and two leg openings.

BACKGROUND

To join together the side parts of diapers and pant diapers, it is today common to use fasteners, such as those available under the trade name Velcro®, that extend from the waistline of the user over the hips. In this way, the diaper or pant diaper acquires a good fit, which is important for its function and to provide an aesthetically pleasing appearance. The Velcro® fastener comprises an elongated strip from which a large number of hook devices project, and a device provided with loops that can include a strip of textile or non-woven material or a surface layer of the diaper or pant diaper. One problem with using strips that extend downwards past the hips of the user is that the lower edges of the strip can cause irritation of the skin by chafing against the leg of the user when he or she moves.

The present invention includes embodiments aimed to solve this problem.

SUMMARY OF THE INVENTION

This aim is achieved according to embodiments of the invention through a diaper or pant diaper with a front section, a rear section, and an intermediate crotch section that has a narrower width than the front and rear sections. A longitudinal line of symmetry extends from the middle of the rear edge of the rear section to the middle of the front edge of the front section. The diaper or pant diaper includes an absorption body that is enclosed between an inner surface layer of liquid-permeable material and an outer surface layer of liquid-impermeable material, whereby the side parts of the front and rear sections can be joined to one another with a refastenable closure by means of a first mechanical join so that the diaper or pant diaper, in the position of use where the side parts are joined to one another in an over-lapping manner, acquires a pants-like configuration with one waist opening and two leg openings characterized in that a band of soft and flexible material, whose one end is permanently attached to the side part of the section of the front or rear section that, when in the position of use, is overlapped by the side part of the other section, is, in the position of use, folded over each edge of the leg opening and attached in a refastenable manner to the outside of the overlapping side part of the mutually joined side parts by means of a second join.

According to one preferred embodiment, each band has a width and placement so that it extends in a cross-sectional direction across the full width of the first mechanical join, and one end of the band is attached to the inner surface layer of the side part of the section of the front or rear section that, in the position of use, is overlapped by the side part of the other section. Alternatively, one end of the band can be attached to the outer surface layer of the side part of the section of the front or rear section that, in the position of use, is overlapped by the side part of the other section.

The diaper can also include a band of soft and flexible material whose one end is permanently attached to the side part of the section of the front or rear section that, in the position of use, is overlapped by the side part of the other section, and that, in the position of use, is folded over each edge of the waist opening and attached by a refastenable closure to the outside of the overlapping side part of the side parts that are joined to one another. Each band can extend from the leg opening to the waist opening of the side part to which the band is permanently attached. The first and second mechanical join can advantageously comprise an interacting hook and loop device. In one advantageous variation, the outer liquid-impermeable surface layer includes an outwards-facing non-woven layer and the band includes a hook device that can be attached to the liquid-impermeable surface layer. The band is preferably made of a non-woven material with a surface weight greater than 30 g/m$^2$. Alternatively, the band can be made of non-woven material, at least one side of which can be covered with layer of foam plastic. In addition, the band can be thicker at the part that extends across the edge of the leg opening when in the position of use of the diaper. In the position of use, each band advantageously extends over the whole length of the associated mechanical join on the inside and/or outside of that join.

BRIEF DESCRIPTION OF THE DRAWINGS

Embodiments of the invention will now be described with reference to the following figures.

DETAILED DESCRIPTION OF EMBODIMENTS OF THE INVENTION

Figure 1:
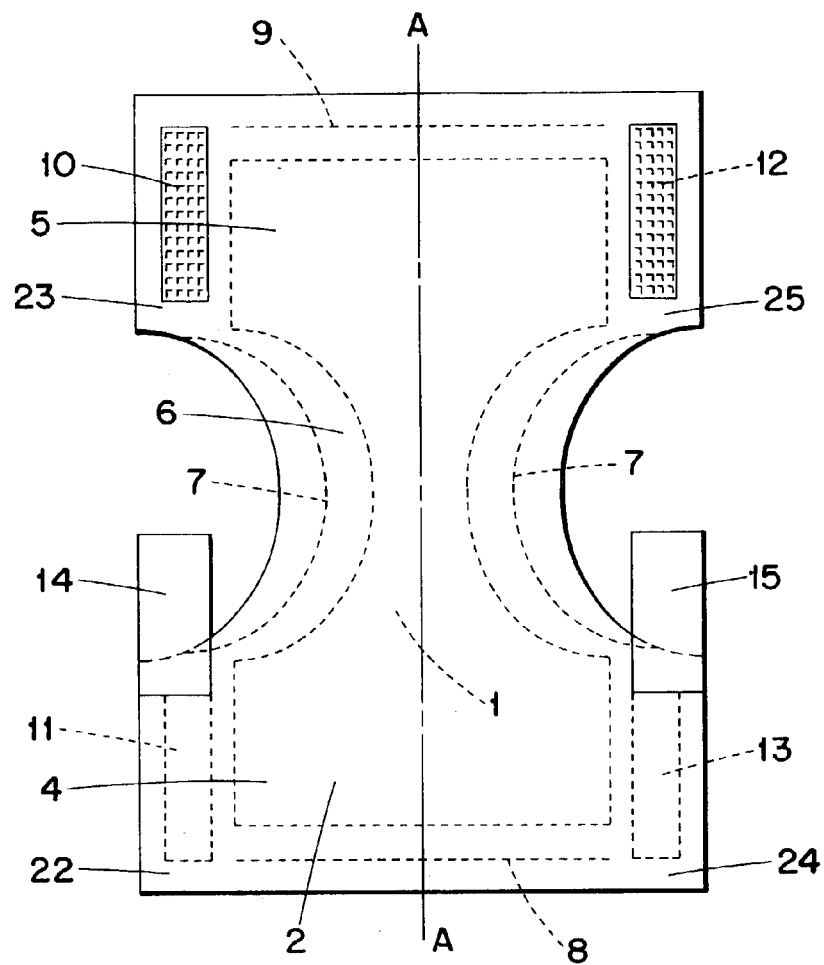
FIG. 1 shows schematically a frontal view of a diaper according to one preferred embodiment of the invention with the inside of the diaper facing the viewer.
Figures 2, 3:
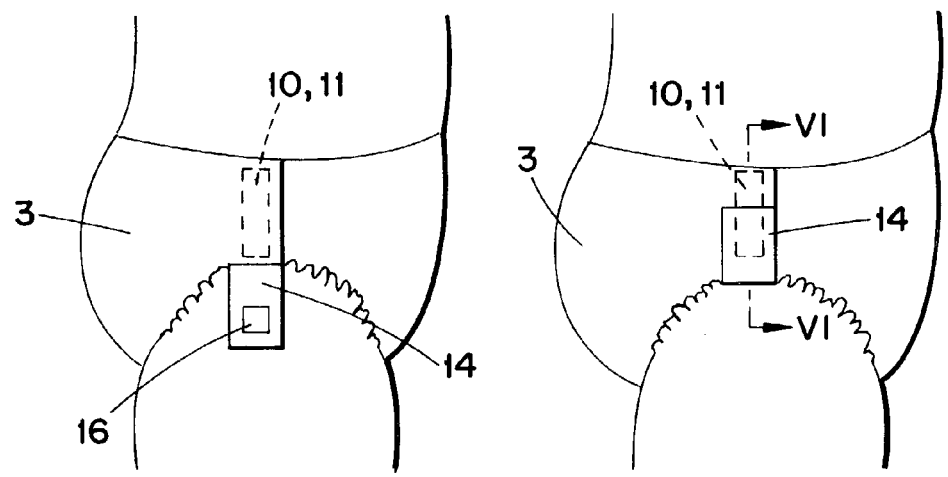
FIG. 2 shows a side view of the diaper according to FIG. 1 with the protective band not brought into place.
FIG. 3 shows a side view as in FIG. 2 with the protective band brought into place.

FIGS. 1–3 show a diaper according to one preferred embodiment of the invention. The diaper includes an absorption body 1 enclosed between an inner, liquid-permeable surface layer 2 and an outer, liquid-impermeable surface layer 3. Surface layers 2 and 3 are joined to one another by suitable means, e.g. gluing or thermal sealing, at parts located outside of the absorption body. In addition, the diaper is divided into a front section 4, a rear section 5, and an intermediate crotch section 6 that is narrower than the front and rear sections. The diaper is divided into two symmetrical mirror images by a longitudinal line of symmetry A—A. The diaper can have the shape of an hour-glass and elongated elastic threads or elastic bands 7 can extend along the tapered sides of the side edges to form the leg elastic. In addition, elastic threads or bands 8 and 9 can extend along the front and back edges respectively of the diaper to form the waist elastic. The elastic elements can be applied in a pre-tensioned state between the surface layers 2,3 and joined to these. FIG. 1 shows the elastic elements in their pre-tensioned state.

So that the side parts 22,23 and 24,25 of the front and rear sections 4,5 respectively of the diaper can be joined to one another, the areas at the long edges of these sections are provided with strips 10,11 and 12,13, respectively, of attachment devices that interact with one another. In the example shown, strips 10,12 are provided with hook devices while strips 11,13 are provided with loop devices into which the hook devices fit. The strips can be trade name Velcro® type devices, or other types of hook and loop devices. As illustrated in FIG. 1, strips 10–13 extend in a lengthwise direction along the greater part of the long edges of the front and rear sections. When the diaper is put in place, the side parts 22,23 and 24,25 of the front and rear sections, respectively, will thus be joined with one another over a large portion of their length, which ensures a good fit for the diaper and allows the fit to be maintained even when the absorption body is filled with discharged liquid. In the embodiment shown, the hook devices are arranged on the strips 10,12 that are attached to the long edge areas of the rear section 5, and the loop devices on the strips 11,13 that are attached to the long edge areas of the front section 4, but a reversed placement of the hook and loop devices is naturally also possible. The strips 10, 12 with the hook devices are suitably attached to the inner surface layer 2 and the strips 11, 13 with the loop devices suitably attached to the outer surface layer 3 so that the side parts 22,23 and 24,25 respectively of the front and rear sections can be joined with one another by overlapping.

In accordance with an embodiment of the invention, bands 14 and 15, respectively, are attached to the side parts 22,24 of the front section, with the bands extending in a cross-sectional direction from the outermost corner of the front section that faces the crotch section and past the corners of the strips 10,11 and 12,13, respectively, which are turned towards the absorption body. These bands are attached to the inner surface layer 2 at the rear section of the side parts of the front section by a suitable means, e.g., gluing or thermal sealing, and extend in a longitudinal direction some way outside the rear boundaries of these side parts towards the side parts 23,25 of the rear section when the diaper is in the flat condition shown in FIG. 1. The bands 14,15 can be made of a soft and flexible material, e.g., non-woven material or a laminate of non-woven material and plastic foam or plastic material.

FIG. 2 shows a schematic side view of the diaper in FIG. 1 as worn by a user. As is evident from this figure, the band 14 extends downwards somewhat at the leg of the user and is provided with a means of attachment 16 so that it can be attached to the outside of the diaper. The means of attachment 16 is of a refastenable type and can include an adhesive coating or a piece of material provided with hooks that interacts with the outer non-woven layer of the outer, liquid-impermeable surface layer 3 or with a piece of material provided with loops attached to the outside of the diaper if the outer surface layer does not have an outer non-woven layer. It is pointed out that the means of attachment 16 will only be subjected to minor loadings during the use of the diaper and that its fastening to the outside of the diaper can therefore be weak. FIG. 3 shows a similar view to FIG. 2 but with the band 14 refastened to the outside of the diaper.

The task of the band 14,15 is to prevent the lower edges of the strips 10,11 respectively 12,13 that are joined to one another from chafing against the leg of the user when he or she moves. To achieve this function, the band can have a certain thickness (>0.2 mm) and can have, therefore, a surface weight greater than 30 g/m², at least within the area that covers the lower edge of the strips 10,11 and 12,13 when these strips are joined to one another. One way of achieving different surface weights for bands 14,15 is to provide them with an extra piece of material within the area that covers the lower edges of the strips 10,11 and 12,13, respectively, when the bands are in place. Such an extra piece of material can naturally be made of a different material than the rest of the band. The band can also be wider than the strips 10–13, although this is not essential.

In one variation, the band 14,15 can be made of a laminate of different materials, e.g. a non-woven material and a foam plastic with a non-woven layer located furthest from the surface layer 2,3. Even a band of textile material can be considered for use.

Figure 4:
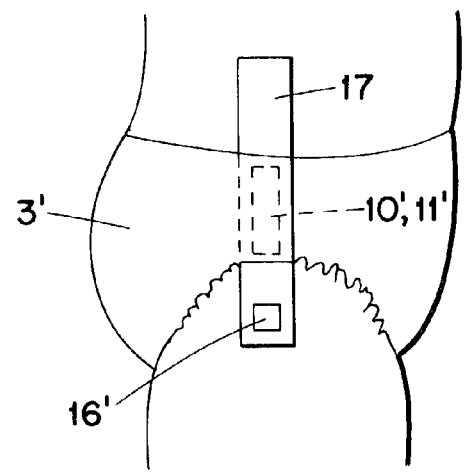
FIG. 4 shows a side view like FIG. 2 of another embodiment of a diaper according to an embodiment of the invention.
Figure 5:
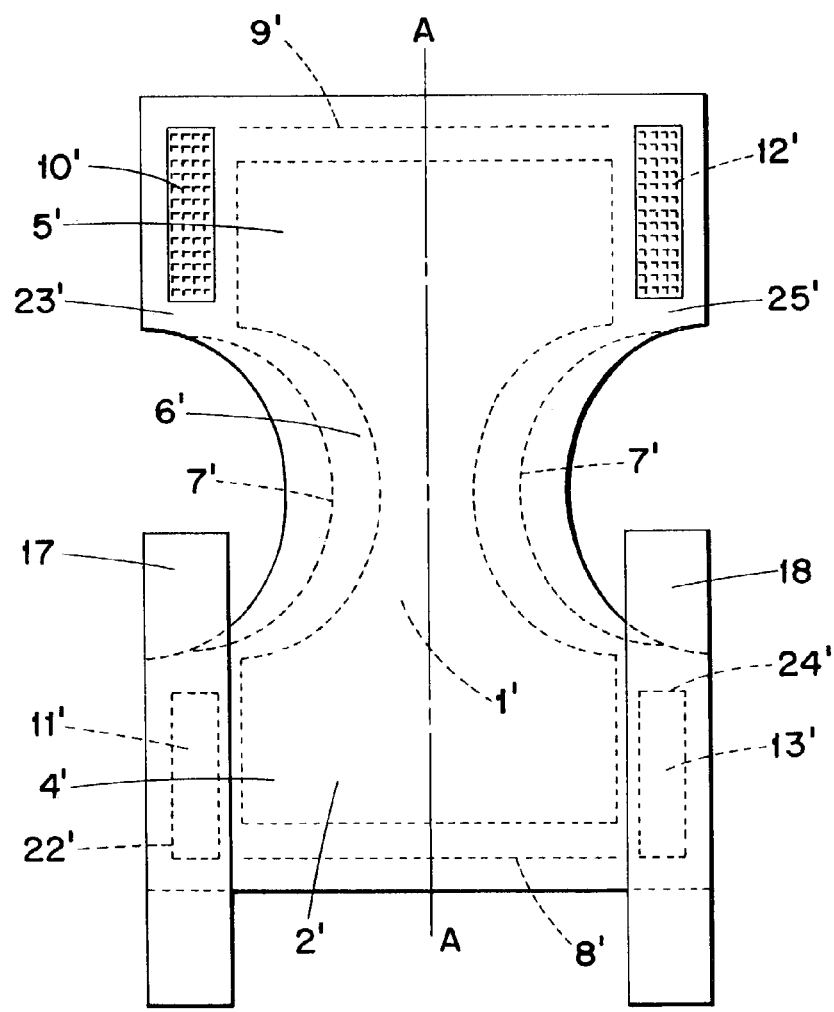
FIG. 5 shows a view like FIG. 1 of another embodiment of a diaper according to an embodiment of the invention.

FIG. 4 shows a similar view to FIG. 2 and FIG. 5 a similar view to FIG. 1 of another embodiment of a diaper according to an embodiment of the invention. This embodiment differs from the embodiment shown with reference to FIGS. 1–3 only in that the bands 17,18 have a different shape than the bands 14,15. In FIG. 4, components that are the same as the equivalent components in FIGS. 1–3 have been given the same reference designation figure with the addition of the prime sign. The bands 17,18 extend along the whole length of the respective long edge area of the front section 4' and also past the front and rear edges of these areas. In addition, bands 17,18 have a length so that the front and rear end parts overlap one another when the bands are folded over the upper and lower edges of the strips 10',11' and 12',13', respectively, that are attached to one another. The means of attachment 16' is thus designed to be attached to the upper part of the band 17 shown in FIG. 4 instead of to the outer side of the diaper.

The present invention solves in a simple and elegant manner the problem that the edges of strips located at the leg and provided with an interacting means of attachment and joined to one another can give rise to chafing against the leg of the user when he or she moves. The strip edges located at the waist line are not associated with the same risk of chafing when a user moves, but there nevertheless exists a certain risk that the edges can chafe when the user bends forwards, backwards or to the side.

The length of the part of the band 14,15 that extends outside of the lower edge of the diaper in place shown in FIG. 2 need not be greater than necessary for the band to be fastened in the folded-in state to the outside of the diaper. However, for aesthetic reasons, it can be appropriate that the band in its applied position extends from the leg opening to the waistband or only extends a small distance from the leg opening in the direction of the waistband. In addition, it can be appropriate to provide this piece of material with rounded edges. To prevent chafing, the fold of the folded-in band need not be positioned directly adjoining the edges of the strips that are joined with one another; it is preferable if the edges of the strips are covered by the band after folding inwards.

Figure 6A:
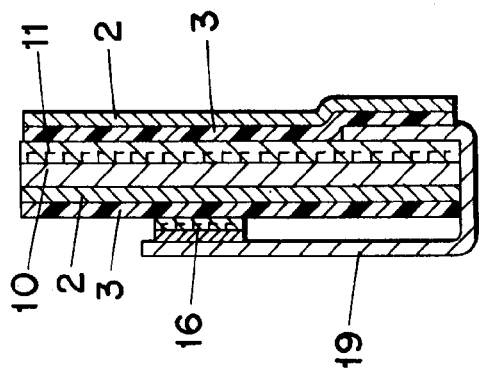
FIG. 6 shows different variations of attachments and extensions of bands according to embodiments of the invention.
Figure 6B:
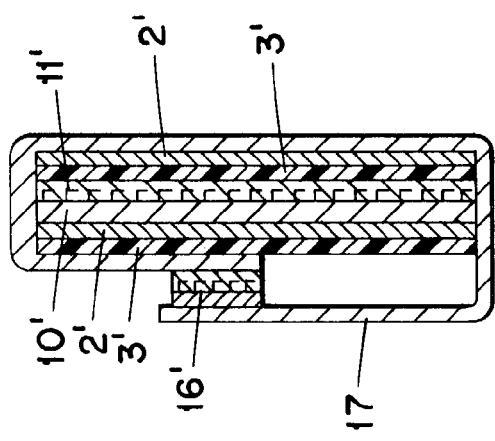
Figure 6C:
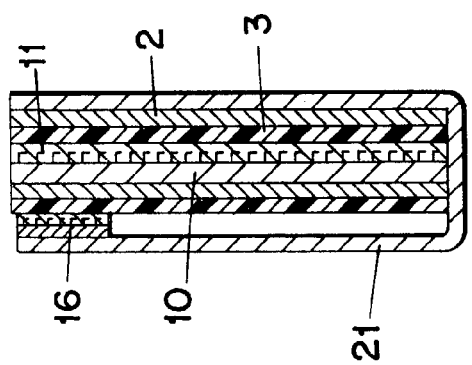
Figure 6D:
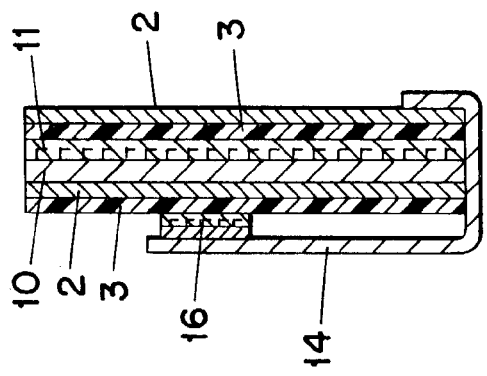
Figure 6E:
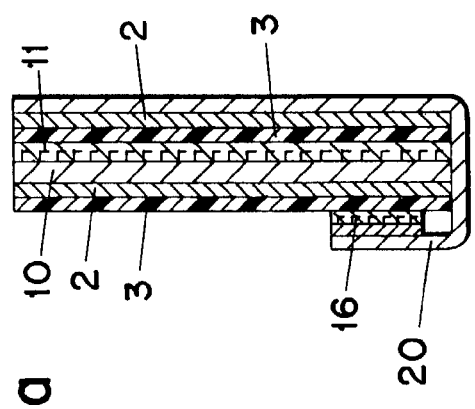

FIG. 6*a* shows a cross-sectional view along the line VI—VI in FIG. 3 and FIG. 6*b* shows an equivalent view through the diaper according to the embodiment shown in FIGS. 4 and 5. FIGS. 6*c*–6*e* show equivalent views of other embodiments of the diaper according to an embodiment of the invention. In all figures except FIG. 6*c*, the bands 14,17, 20 and 21 are attached to the inner surface layer 2 of the overlapping side part of the diaper, while the band 19 in the embodiment shown in FIG. 6*c* is attached to the outer surface layer 3 of the overlapping side part of the diaper. Naturally, even the bands in FIGS. 6*a,b,d* and *e* can instead be attached to the outer surface layer of the overlapping side part. As is evident from the figures, the bands can also have different extensions in height, but it is preferable if they either extend over the first mechanical join 10,11 or only past the upper or lower edge of this join, as shown schematically in FIGS. 6*e* and 6*d*, respectively. In addition, the attached end of the band can extend in height along the whole length of the join 10,11 as shown in FIGS. 6*b,d* and *e*, or only over a part of this, as shown in FIGS. 6*a* and *c*.

The inner, liquid-permeable surface layer 2 of the diaper can comprise a, non-woven material or a non-woven laminate. All other materials used for a inner, liquid-permeable surface layer of diapers and similar absorbing articles can also be used, such as, for example, perforated plastic films.

The outer liquid-impermeable surface layer is preferably made of a laminate of vapour-permeable plastic film and a non-woven material, preferably one that can act as loops for the hooks of the chosen strip provided with hooks, whereby separate strips 11,13 provided with loops are no longer needed. All other materials used for the liquid-impermeable surface layer of diapers and similar absorbing articles can naturally also be used.

The absorption body is preferably made of one or several layers of cellulose stuffing with or without the addition of particles of so-called super-absorbent material. Other types of fibre, such as binder fibre, can be mixed in the cellulose stuffing. In addition, layers with good permeability capabilities, e.g. hydrophobic wadding, can be included in the absorption body. All other material that is used in absorption body for absorbing articles, for example foam plastic, can naturally also be used.

In the described embodiments, the absorption body, like the outer covering of the diaper, can have the shape of an hour-glass, but it is naturally possible to give the absorption body another shape, for example, a rectangular form.

The embodiments described herein illustrate diapers, but the invention can also be applied to pant diapers that can be opened, whereby the strips provided with attachment devices are joined to one another and the bands that cover the edges of the strips are attached to the outside of the pant diapers in conjunction with manufacture of the pants diapers and are supplied in an assembled state. The side parts, i.e., those parts of the outer covering that extend in a sideways direction outside of the absorption body, are preferably elasticized for a pant diaper. Also, diapers in accordance with embodiments of the invention can be provided with elasticized side panels.

The described embodiments can naturally be modified within the scope of the invention. For example, the corners of the strips can be rounded to further reduce the risk of chafing. The outer surface layer need not be liquid-impermeable over the whole of its surface but can have that part of the outer surface that does not cover the absorption body perforated or consisting of material that is very permeable to air, e.g., a net material. If the diaper or pant diaper has elasticized side panels, these can be made of separate panels of elasticized material or elasticized parts of one or both surface layers. The mechanical first join need not comprise hook and loop devices but can be composed of other types of mechanical join, such as buttons and button holes, snap-in fastenings, etc. In addition, the band need not comprise separate pieces of material but can be composed of surface layer parts that remain after punching out the leg openings.

Although only preferred embodiments are specifically illustrated and described herein, it will be appreciated that many modifications and variations of the present invention are possible in light of the above teachings and within the purview of the appended claims without departing from the spirit and intended scope of the invention.

The invention claimed is:

1. Diaper or pant diaper comprising:
   a front section, a rear section, and an intermediate crotch section having a narrower width than the front and rear sections, and a longitudinal line of symmetry extending from a middle of a rear edge of the rear section to a middle of a front edge of the front section,
   an absorption body enclosed between an inner surface layer of liquid-permeable material and an outer surface layer of liquid-impermeable material whereby side parts of the front section can be joined to side parts of the rear section by refastenable closures each having a first mechanical join so that the diaper or pant diaper, in a position of use where the side parts are joined to one another in an over-lapping manner, acquires a pants-like configuration with one waist opening and two leg openings, and
   a band of soft and flexible material, one end of which is permanently attached to the side part of one of the front or rear sections, which side part, when in the position of use, is overlapped by the side part of the other of the front or rear section such that the one side part is between the other side part and a wearer of the diaper or pant diaper,
   wherein, in the position of use, the band is folded over an upper edge and a lower edge of the overlapping side parts and refastenable to the outside of the overlapping side part of the mutually joined side parts by means of a second join.

2. The diaper or pant diaper according to claim 1, wherein each band has a width and placement such that in a cross-sectional direction each band extends over a whole width of the first mechanical join.

3. The diaper or pant diaper according to claim 1, wherein one end of the band is attached to the inner surface layer of the side part of the section of the front or rear section that, in the position of use, is overlapped by the side part of the other section.

4. The diaper or pant diaper according to claim 1, wherein one end of the band is attached to the outer surface layer of the side part of the section of the front or rear section that, in the position of use, is overlapped by the side part of the other section.

5. The diaper or pant diaper according to claim 1, wherein a band of soft and flexible material, having one end permanently attached to the side part of the section of the front or rear section that, in the position of use, is overlapped by the side part of the other section, is, in the position of use, folded over each edge of the waist opening and refastenable to the outside of the overlapping side part of the mutually joined side parts.

6. The diaper or pant diaper according to claim 5, wherein each band extends from the leg opening to the waist opening of the side part to which the band is permanently attached.

7. The diaper or pant diaper according to claim 1, wherein the first mechanical join comprises interacting hook and loop devices.

8. The diaper or pant diaper according to claim 1, wherein the second mechanical join comprises interacting hook and loop devices.

9. The diaper or pant diaper according to claim 1, wherein the liquid-impermeable surface layer includes an outwards facing non-woven layer and that the band includes hook devices than can be attached to the liquid-impermeable surface layer.

10. The diaper or pant diaper according to claim 1, wherein the band is made of non-woven material with a surface weight greater than 30 g/m$^2$.

11. Diaper or pant diaper comprising:
a front section, a rear section, and an intermediate crotch section having a narrower width than the front and rear sections, and a longitudinal line of symmetry extending from a middle of a rear edge of the rear section to a middle of a front edge of the front section,
an absorption body enclosed between a inner surface layer of liquid-permeable material and an outer surface layer of liquid-impermeable material whereby side parts of the front and rear sections can be joined to one another by refastenable closure by means of a first mechanical join so that the diaper or pant diaper, in a position of use where the side parts are joined to one another in an over-lapping manner, acquires a pants-like configuration with one waist opening and two leg openings, and
a band of soft and flexible material, whose one end is permanently attached to the side part of one of the front or rear section that, when in the position of use, is overlapped by the side part of the other of the front or rear section,
wherein, in the position of use, the band is folded over an upper edge and a lower edge of the overlapping side parts and refastenable to the outside of the overlapping side part of the mutually joined side parts by means of a second join,
wherein the band is made of non-woven material, one side of which is at least partly covered with a layer of foam plastic.

12. Diaper or pant diaper comprising:
a front section, a rear section, and an intermediate crotch section having a narrower width than the front and rear sections, and a longitudinal line of symmetry extending from a middle of a rear edge of the rear section to a middle of a front edge of the front section,
an absorption body enclosed between a inner surface layer of liquid-permeable material and an outer surface aver of liquid-impermeable material whereby side parts of the front and rear sections can be joined to one another by refastenable closure by means of a first mechanical join so that the diaper or pant diaper, in a position of use where the side parts are joined to one another in an over-lapping manner, acquires a pants-like configuration with one waist openinq and two leg openings, and
a band of soft and flexible material, whose one end is permanently attached to the side part of one of the front or rear section that, when in the position of use, is overlapped by the side part of the other of the front or rear section,
wherein, in the position of use, the band is folded over an upper edge and a lower edge of the overlapping side parts and refastenable to the outside of the overlapping side part of the mutually joined side parts by means of a second join,
wherein the band is thicker in a part of the band which, in the position of use, extends over the edge of the leg opening.

13. Diaper or pant diaper according to claim 1, wherein each band, in the position of use, extends over the whole length of the associated first mechanical join on the inside and/or outside of this join.

14. Diaper or pant diaper comprising:
a front section, a rear section, and an intermediate crotch section having a narrower width than the front and rear sections, and a longitudinal line of symmetry extending from a middle of a rear edge of the rear section to a middle of a front edge of the front section,
an absorption body enclosed between an inner surface layer of liquid-permeable material and an outer surface layer of liquid-impermeable material whereby side parts of the front section can be joined to side parts of the rear section by refastenable closures each having a first mechanical join so that the diaper or pant diaper, in a position of use where the side parts are joined to one another in an over-lapping manner, acquires a pants-like configuration with one waist opening and two leg openings, and
a band of soft and flexible material, one end of which is permanently attached to the side part of one of the front or rear sections, which side part, when in the position of use, is overlapped by the side part of the other of the front or rear section such that the one side part is between the other side part and a wearer of the diaper or pant diaper,
wherein, in the position of use, the band is folded over at least a lower edge of one of the leg openings and refastenable to the outside of the overlapping side part of the mutually joined side parts by means of a second join.

15. Diaper or pant diaper comprising:
a front section, a rear section, and an intermediate crotch section having a narrower width than the front and rear sections, and a longitudinal line of symmetry extending from a middle of a rear edge of the rear section to a middle of a front edge of the front section,
an absorption body enclosed between an inner surface layer of liquid-permeable material and an outer surface layer of liquid-impermeable material whereby side parts of the front section can be joined to side parts of the rear section by refastenable closures each having a first mechanical join so that the diaper or pant diaper, in a position of use where the side parts are joined to one another in an over-lapping manner, acquires a pants-like configuration with one waist opening and two leg openings, and a band of soft and flexible material, one end of which is permanently attached to the side part of one of the front or rear sections, which side part, when in the position of use, is overlapped by the side part of the other of the front or rear section such that the one side part is between the other side part and a wearer of the diaper or pant diaper, wherein, in the position of use, the band extends in a vertical direction and is folded over an edge of one of the leg openings and refastenable to the outside of the overlapping side part of the mutually joined side parts by means of a second join.

* * * * *